United States Patent [19]
Knöfel et al.

[11] Patent Number: 5,648,520
[45] Date of Patent: Jul. 15, 1997

[54] FRACTIONATION AND PURIFICATION OF AROMATIC POLYAMINE AND THE USE THEREOF

[75] Inventors: Hartmut Knöfel, Odenthal; Michael Brockelt, Leverkusen, both of Germany

[73] Assignee: Bayer Aktiengesellschaft, Leverkusen, Germany

[21] Appl. No.: 623,286

[22] Filed: Mar. 28, 1996

[30] Foreign Application Priority Data

Apr. 7, 1995 [DE] Germany ............... 19513163.0

[51] Int. Cl.$^6$ ............................................. C07C 209/86
[52] U.S. Cl. ............. 560/347; 564/315; 564/331; 564/332; 564/333; 564/334; 564/437; 564/450; 564/451
[58] Field of Search ............... 564/315, 331, 564/332, 333, 334, 437, 450, 451; 560/347

[56] References Cited

U.S. PATENT DOCUMENTS

| | | | |
|---|---|---|---|
| 4,087,459 | 5/1978 | Knöfel et al. | 564/331 |
| 4,914,236 | 4/1990 | Knöfel et al. | 564/334 |
| 4,924,028 | 5/1990 | Knofel et al. | 564/331 |
| 5,196,591 | 3/1993 | Knöfel et al. | 564/331 |
| 5,359,141 | 10/1994 | Knofel et al. | 564/331 |

FOREIGN PATENT DOCUMENTS

| | | |
|---|---|---|
| 2238319 | 2/1973 | Germany. |
| 1170619 | 11/1969 | United Kingdom. |

OTHER PUBLICATIONS

H. Becker et al "Organikum" 1976, Veb Destscher Verlag der Wissenschaften, Berlin XP002005624, pp. 74–82.

*Primary Examiner*—Richard L. Raymond
*Attorney, Agent, or Firm*—Joseph C. Gil

[57] ABSTRACT

The invention relates to a process for the fractionation and purification of aromatic polyamine mixtures and the use thereof.

10 Claims, 4 Drawing Sheets

FRACTIONATION AND PURIFICATION OF AROMATIC POLYAMINE AND THE USE THEREOF

BACKGROUND OF THE INVENTION

The present invention relates to a process for the fractionation and purification of aromatic polyamine mixtures and the use of the mixtures. Numerous patent applications and patents describe the preparation of aromatic polyamines and polyamine mixtures, in particular of the diphenylmethane series, and also the use of these products. These publications place great importance on the use of these products as raw materials for manufacturing isocyanates, generally by reacting the polyamine mixtures with phosgene by the known methods generally practiced.

However, in many cases the resulting isocyanates or isocyanate mixtures arise in forms and compositions not appropriate to their preferred further use in the isocyanate stage, which must first be converted into the appropriate usable form by, in some cases costly, working-up and separation processes. Suitable precursor polyamines which can be converted at less expense into the isocyanate forms to be used frequently give rise to process engineering problems, are completely inaccessible or are economically unattractive to manufacture.

An example is 4,4'-diisocyanatodiphenylmethane, which is important in the manufacture of high-grade polyurethane materials, the precursor amine of which is generally obtainable from aniline and formaldehyde only jointly with isomers, in particular the 2,4'-isomer, and higher-functional polyamines. Although these constituents are the foundation for isocyanates which are equally in demand, the raw isocyanates are not readily separated into those isocyanates or isocyanate mixtures which are suitable for further use. Generally, this involves first separating some of the binuclear compounds from the remainder. The 4,4'-diisocyanatodiphenylmethane is then liberated from the other isomers from the binuclear fraction in a second distillation step which requires many separation stages.

The 2,4'-isomer in enriched form has recently itself acquired increasing importance as a raw material for polyurethane and it is only with considerable distillation effort that it can be enriched by comparison with the 4,4'-isomer and liberated from the 2,2'-isomer which is optionally present.

Isomer separation processes or enrichment processes within the fraction comprising higher-nuclear homologues or higher-functional constituents of amines and of isocyanates of the diphenylmethane series are virtually unknown.

4,4'-diaminodiphenylmethane is also gaining ground increasingly as a raw material for di-(4-isocyanatocyclohexyl) methane, the nucleus-hydrogenated form of 4,4'-diisocyanatodiphenylmethane, wherein it is very costly to prepare suitable aromatic polyamine mixtures for the hydrogenation stage having as high a 4,4'-diaminodiphenylmethane content as possible with simultaneously as low a proportion of 2,4'-diaminodiphenylmethane as possible.

It is known that amines can in some cases be separated by partially converting them into their salts, wherein, inter alia, use is made of the different base strengths. These are generally monoamines having widely differing base strengths. Such disproportionation effects have also already been described in two-phase systems in respect of aromatic polyamine mixtures, in particular of the diphenylmethane series (German Auslegeschriften 2,238,319 and 2,528,694).

As a result of the numerous components present in such a mixture, whose amino groups differ hardly at all in terms of type—virtually all are arylamino groups—the effects are not particularly sizeable or pronounced in terms of being of interest for direct use with simple means.

The object was to provide a process which enables aromatic polyamine mixtures to be fractionated and/or purified in simple manner such that isomers arise in a pure or an enriched form.

DESCRIPTION OF THE INVENTION

Figure 1:
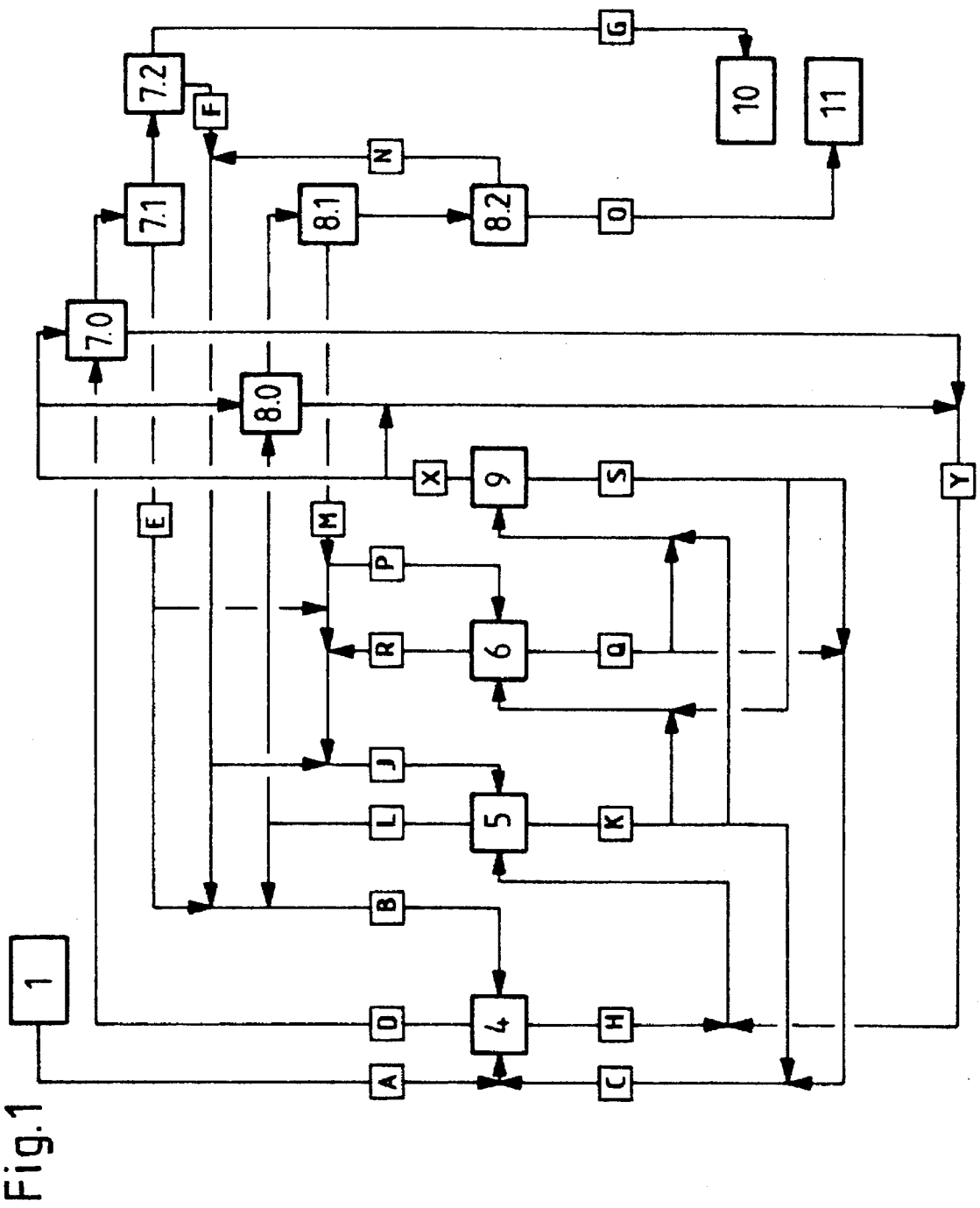
FIGS. 1 through 4 represent flow diagrams for various embodiments of the present invention.

It has been possible to achieve the above noted object by means of the process according to the invention, which when carried out according to the invention obtains a surprisingly high separation efficiency in the fractionation of aromatic polyamine mixtures, in particular of the diphenylmethane series, and does so in a manner which far outperforms the known effects of the prior art.

Other polyamine mixtures of various compositions are obtained during the fractionation according to the invention of aromatic polyamine mixtures. These derived polyamine mixtures may be of types which are accessible only at very great cost by known synthetic routes. They may also be polyamine mixtures which are more suitable for simpler manufacture of isocyanates than those which are known and are readily amenable to industrial preparation, in that, for example, by correspondingly enriching isomers in the amine stage they anticipate difficult isomer separations in the isocyanate stage. Such mixtures may also be completely novel polyamine mixtures because they cannot be realized using the prior art, and may lead to completely novel isocyanates.

On the other hand, the process according to the invention may be used to obtain from any—thus including recycled—polyamine mixtures product fractions which are to standard or which conform to the starting polyamines, despite the polyamine mixtures differing from the polyamines or isocyanates originally utilized as a result of impurities or non-static, i.e. selective, losses of some components during recycling.

Finally, the process according to the invention may be used to co-fractionate synthesis-related by-products and intermediates which are undesirable in the end product, and to impoverish them in one product fraction and accordingly enrich them in another, optionally to transfer them out in an independent fraction.

The present invention relates to a broadly applicable process which is able to achieve the object of fractionating and purifying aromatic di- and polyamine mixtures, in particular of the diphenylmethane series. The present invention provides a process for the fractionation and purification of aromatic polyamine mixtures, in particular polyamine mixtures of the diphenylmethane series, which is characterized in that a) the polyamine starting mixture (A) is distributed, with intermixing of the phases, in a two-phase system comprising (i) a hydrophobic solvent phase (B) which comprises substantially hydrophobic solvent and optionally an aromatic auxiliary amine which is virtually insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) comprising substantially water, a strong acid and auxiliary amine present at least in part in the salt form, and optionally polyamines present at least in part in the salt form, with the use as an aid of an extraction stage (4) operating on the countercurrent principle, in that the starting polyamine mixture is introduced into the extraction stage (4) by way of the aqueous phase, and the organic phase (D) leaving the extraction stage (4) is, b) optionally at least in part by way of an interposed extraction stage (3) and/or c) optionally with separation of a partial stream upstream or downstream of the extraction stage (3) which is optionally passed through and return of the separated partial stream to the extraction stage (4) by way of an extraction stage (2) positioned upstream, d) separated in a multi-stage distillation (7.1), (7.2) into a first, recycled fraction (E) comprising substantially hydrophobic solvent and optionally auxiliary amine, a second fraction (F) comprising substantially auxiliary amine and optionally hydrophobic solvent, and a distillation residue (G) comprising substantially a first polyamine fraction, and e) the aqueous phase (H) leaving the extraction stage (4) is guided into an extraction stage (5) in which there takes place on the countercurrent extraction principle an extraction of the aqueous phase with a solvent phase (J) comprising hydrophobic solvent and auxiliary amine, wherein there results the aqueous phase (K) which is impoverished as to polyamine, and f) the organic phase (L) arising in the extraction stage (5) is at least in part, optionally after passing through a washing stage (8.0), separated in a multi-stage distillation (8.1), (8.2) into a first fraction (M) comprising substantially hydrophobic solvent and optionally proportions of auxiliary amine, and a second fraction (N) comprising substantially auxiliary amine and optionally proportions of hydrophobic solvent, and a distillation residue (O) comprising substantially a second polyamine fraction, and g) the aqueous phase (K) arising in the extraction stage (5) is at least in part, h) optionally at least in part by way of an interposed distillation stage (9), i) guided into an extraction stage (6) and is extracted in countercurrent with an organic phase (P) comprising substantially hydrophobic solvent and optionally as a maximum sufficient auxiliary amine such that there results in (6) an aqueous phase (Q) which, compared with the aqueous phase (K) utilized, is impoverished as to arylamine and which is, k) optionally at least in part by way of an interposed distillation stage (9), l) combined with the optionally present residues of (Q) and (K) and is recycled as stream (C), in that stream (C) is, m) optionally at least in part by way of an interposed extraction stage (3) and/or n) optionally at least in part first by way of an extraction stage (2) positioned upstream and then by way of an optionally present extraction stage (3), o) returned to the extraction stage (4) and is there recycled, optionally after the addition of water and/or auxiliary amine, as stream (C), and p) the organic phase (R) arising in the extraction stage (6) is, optionally after the addition of further organic phase from stream (S), comprising substantially auxiliary amine, supplied to the extraction stage (5) as extraction agent phase (J).

The various capital letters and numbers appearing above and in the following description refer to the elements and streams from the drawings.

The recycled stream (C) exhibits a higher degree of protonation than the aqueous phase (K) leaving the extraction stage (4), optionally up to 100%.

The process is preferably carried out such that b) the organic phase (D) arising in the extraction stage (4) is at least in part extracted in countercurrent with at least a part volume of stream (C) in an interposed extraction stage (3) and/or is extracted in countercurrent with at least a part volume of the aqueous phase (Z) arising in the optionally present extraction stage (2) positioned upstream, the aqueous phase (U) resulting in the interposed extraction stage (3) is supplied to the extraction stage (4), and the organic phase (V) arising in the interposed extraction stage (3) is supplied to the working-up stage (7).

The process according to the invention is particularly preferably carried out such that c) a partial stream of the organic phase (D) leaving the extraction stage (4) and/or a partial stream of the organic phase leaving the optionally present interposed extraction stage (3) is separated and is extracted in countercurrent in an extraction stage (2) positioned upstream with a part volume, preferably with the total volume, of the aqueous phase available as stream (C), the organic stream (W) utilized in the extraction stage (2) is dimensioned such that there takes place in (2) as extensive a transfer as possible of the polyamine contained in the said organic stream into the aqueous phase, the aqueous phase (Z) resulting in the extraction stage (2) positioned upstream is, optionally after the addition of water from stream (Y) and/or auxiliary amine, supplied at least in part to the extraction stage (3) and the organic phase, impoverished as to polyamine, which arises in the extraction stage (2) positioned upstream is supplied to the extraction stage (4).

A further improved and preferred embodiment of the process according to the invention is that k) before its recycling, the aqueous phase (K) leaving the extraction stage (5) is at least in part, and/or before its recycling the aqueous phase (Q) leaving the extraction stage (6) is at least in part liberated by distillation (9) from a part (X) of the water contained therein, the latter is optionally used for washing (7.0) that part of the organic phase (D) leaving the extraction stage (4) and/or of the organic phase (V) leaving the extraction stage (3), which is/are supplied to the working-up (7.1), (7.2) by distillation, and/or for washing (8.0) that part of the organic phase (L) leaving the extraction stage (5), which is supplied to the working-up (8.1), (8.2) by distillation, for the purpose of removing traces of acid, the water (Y) arising thereby is returned at a suitable point into the aqueous phase, the resulting concentrated aqueous phase is combined with the optionally remaining residues of (K) and (Q) and is supplied to recycling as stream (C).

More particularly, the present invention, in its broadest embodiment, is directed to a process for the fractionation and purification of aromatic polyamine mixtures, in particular of polyamine mixtures of the diphenylmethane series, comprising:

a) mixing the polyamine starting mixture (A) in a first extraction stage (4) with a two-phase system comprising
  (i) a hydrophobic solvent phase (B) which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) consisting essentially of water, a strong acid and auxiliary amine present at least in part in the salt form, and optionally polyamines present at least in part in the salt form, with said first extraction stage (4) operating on the countercurrent principle, and wherein said polyamine starting mixture (A) is introduced into said first extraction stage with said aqueous phase (C), with a first aqueous phase (H) and a first organic phase (D) exiting said first extraction stage (4), b) distilling said first organic phase (D) in a first multi-stage distillation (7.1), (7.2) into i) a first, recycled fraction (E) consisting essentially of hydrophobic solvent and optionally auxiliary amine, ii) a second, recycled fraction (F) consisting essentially of auxiliary amine and optionally hydrophobic solvent, and iii) a distillation residue (G) consisting essentially of a first polyamine fraction, c) extracting said first aqueous phase (H) in a second extraction stage (5) with a solvent phase (J) consisting essentially of hydrophobic solvent and auxiliary amine, said second extraction stage (5) operating on the countercurrent principle, with i) a second aqueous phase (K), said second aqueous phase being reduced in polyamine content and ii) a second organic phase (L) exiting said second extraction stage (5), d) separating at least a portion of said second organic phase (L) in a second multi-stage distillation (8.1), (8.2) into i) a first fraction (M) consisting essentially of hydrophobic solvent and optionally proportions of auxiliary amine, ii) a second fraction (N) consisting essentially of auxiliary amine and optionally proportions of hydrophobic solvent, and iii) a distillation residue (O) consisting essentially of a second polyamine fraction, f) extracting at least a portion of said second aqueous phase (K) in a third extraction stage (6) with an organic phase (P) consisting essentially of hydrophobic solvent and optionally auxiliary amine, said third extraction stage (6) operating on the countercurrent principle, with i) a third aqueous phase (Q), said third aqueous phase being reduced in amine content and ii) a third organic phase (R) exiting said third extraction stage (6), g) recycling said third aqueous phase (Q) as at least a portion of stream (C), and h) recycling said third organic phase (R) to said second extraction stage (5) as at least a portion of solvent phase (J).

Aniline is preferably utilized as the auxiliary amine, and a polyamine mixture such as arises during acid-catalyzed aniline/formaldehyde condensation is preferably utilized as the polyamine mixture of the diphenylmethane series.

The polyamine mixtures treated in this way, thus the fractions generated by the process according to the invention, are used to manufacture the corresponding aromatic polyisocyanate mixtures and to manufacture polyurethane plastics.

The fractions generated by the process according to the invention may moreover be used to prepare the corresponding nucleus-hydrogenated polyamines or as cross-linking agents and as epoxy hardeners.

The corresponding polyisocyanates prepared from the fractionated polyamine mixtures are preferably utilized to manufacture polyurethane foams.

Examples of starting mixtures are, for example, technical grade arylamine mixtures such as arise from the starting compounds during manufacture or such as arise during recovery.

Examples of starting arylamine mixtures for the fractionation and purification whereof the process according to the invention is particularly suitable are:

1. polyamine mixtures of the diphenylmethane series, such as occur during condensation and acid-catalyzed rearrangement of aniline with formaldehyde,
2. polyamine mixtures of the diphenylmethane series such as arise during acid-catalyzed condensation of substituted anilines with formaldehyde,
3. polyamine mixtures of the diphenylmethane series such as arise during co-condensation of substituted anilines with one another and/or with aniline with formaldehyde,
4. polyamine mixtures of the diphenylmethane series such as arise during condensation, including co-condensation, of substituted anilines and/or aniline with aldehydes and/or ketones,
5. polyamine mixtures of the diphenylmethane series such as occur during the nitration and subsequent reduction of di- and/or polyarylmethanes; the term polyarylmethanes is in this instance understood to refer to the benzyl homologues of diphenylmethane particularly,
6. polyamine mixtures of the diphenylmethane series such as occur during condensation of monoaryl monoamines (e.g. aniline, substituted anilines) and/or monoaryl diamines (phenylene-diamines, substituted phenylene-diamines) with aldehydes, ketones in particular formaldehyde, and acid-catalyzed rearrangement and
7. polyamine mixtures of the triphenylmethane series such as occur, for example, during the nitration and subsequent reduction of triphenylmethane, in particular alkyl-substituted triphenylmethanes and the higher-nuclear, in particular benzyl, homologues thereof.

The hydrophobic solvents which are utilized are inert solvents within the boiling point range 30° to 280° C., preferably 80° to 200° C., such as, for example, chlorobenzene, dichlorobenzene, benzene, toluene, ethylbenzene, cumene, xylene, dichloroethane, chloroform and carbon tetrachloride. Xylenes, that is to say technical grade xylene mixtures, in particular o-xylene, toluene, ethylbenzene, cumene and chlorobenzene are preferably utilized. Solvents which exhibit a good dissolving power in respect of the polyamine mixtures used are preferably used.

The acids used are water-soluble proton acids having a pKA value of less than 2.5, preferably less than 1.5. Examples are hydrochloric acid, hydrobromic acid, sulfuric acid, trifluoroacetic acid, methanesulphonic acid or phosphoric acid. Hydrochloric acid and methanesulphonic acid are preferably used. The acids named may also be used in mixture with acid or neutral salts of such acids, such as, for example, the corresponding ammonium salts or equally the corresponding alkali metal salts. The named acids are not used in free form but are present in the circulation system according to the invention in the form of the corresponding ammonium salts of the bases present in the aqueous circulation system. They are generally polyamine mixtures of the same type as the starting mixtures and or the auxiliary amines which are used.

Monoarylamines, such as, for example, aniline and/or aniline derivatives substituted in the ring (nucleus) and/or on the nitrogen atom, are generally used as the auxiliary amine.

Primary anilines are preferably used, with aniline particularly preferred.

The process according to the invention may be carried out both batchwise and continuously. A preferred embodiment is the continuous mode, in which the process is carried out in all stages under the pressure inherent in the system and preferably in an inert gas atmosphere (nitrogen).

The process according to the invention may be repeated with each of the product fractions arising in order to increase the enrichment or corresponding impoverishment effect.

Figure 2:
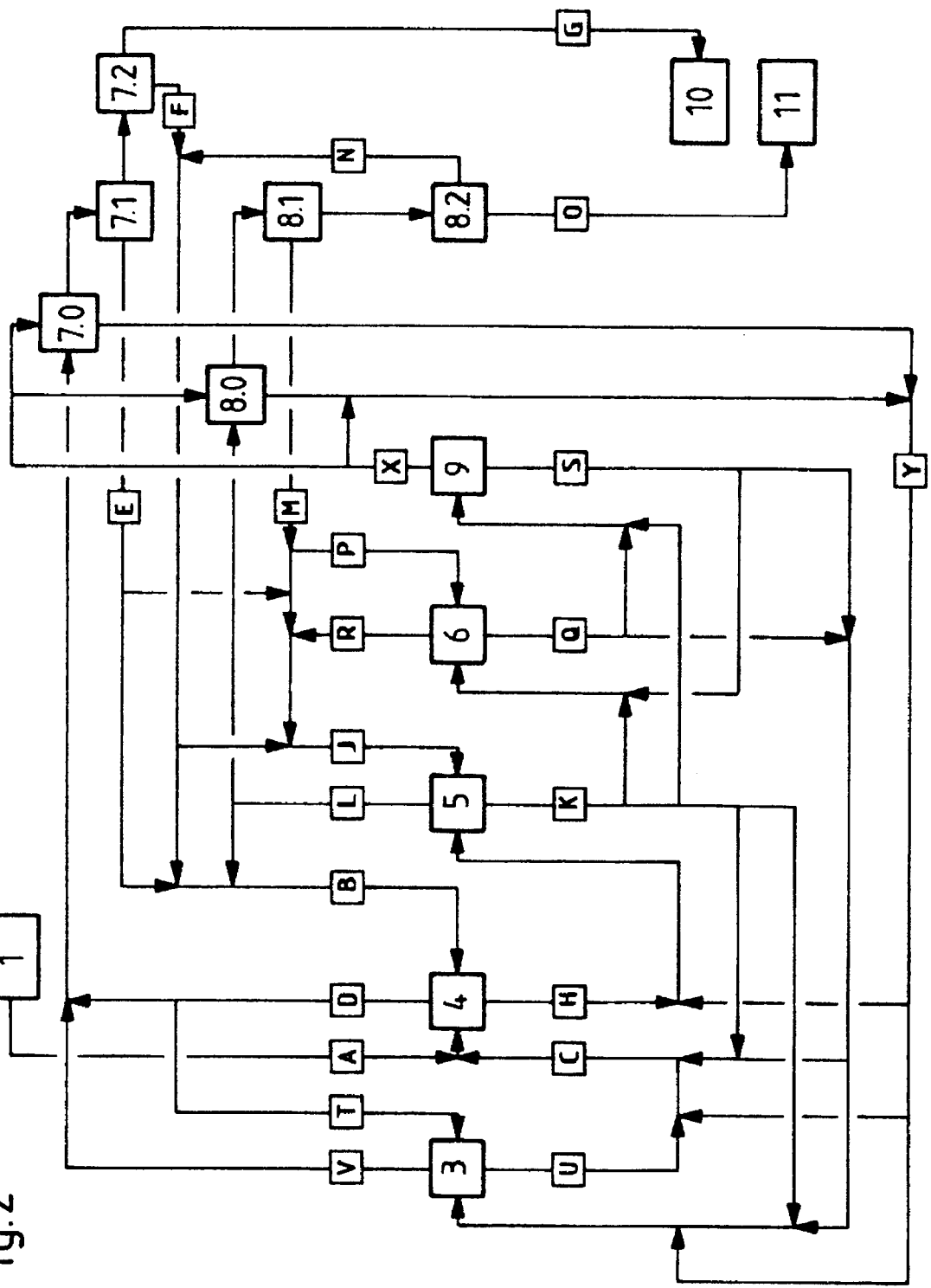
Figure 3:
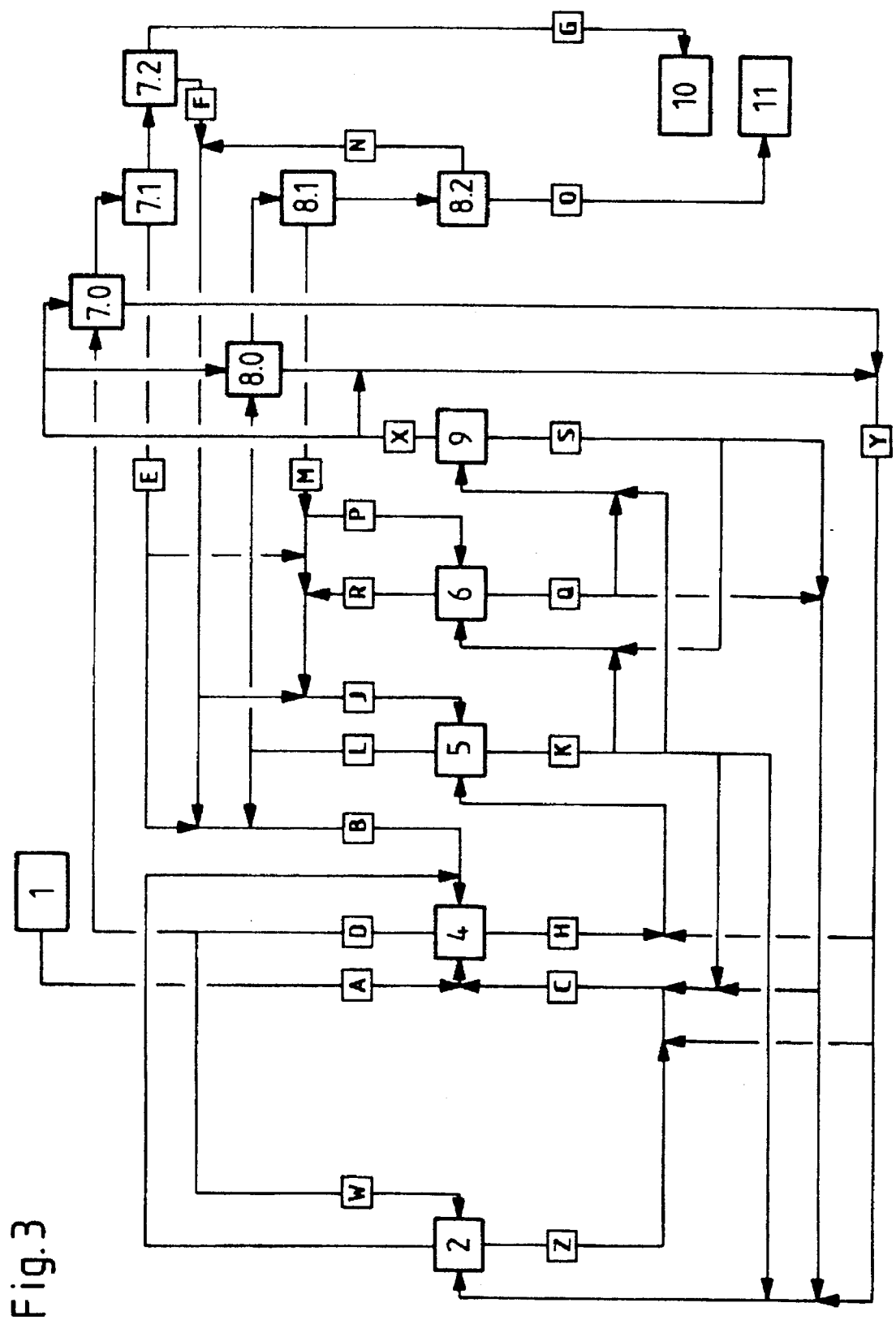
Figure 4:
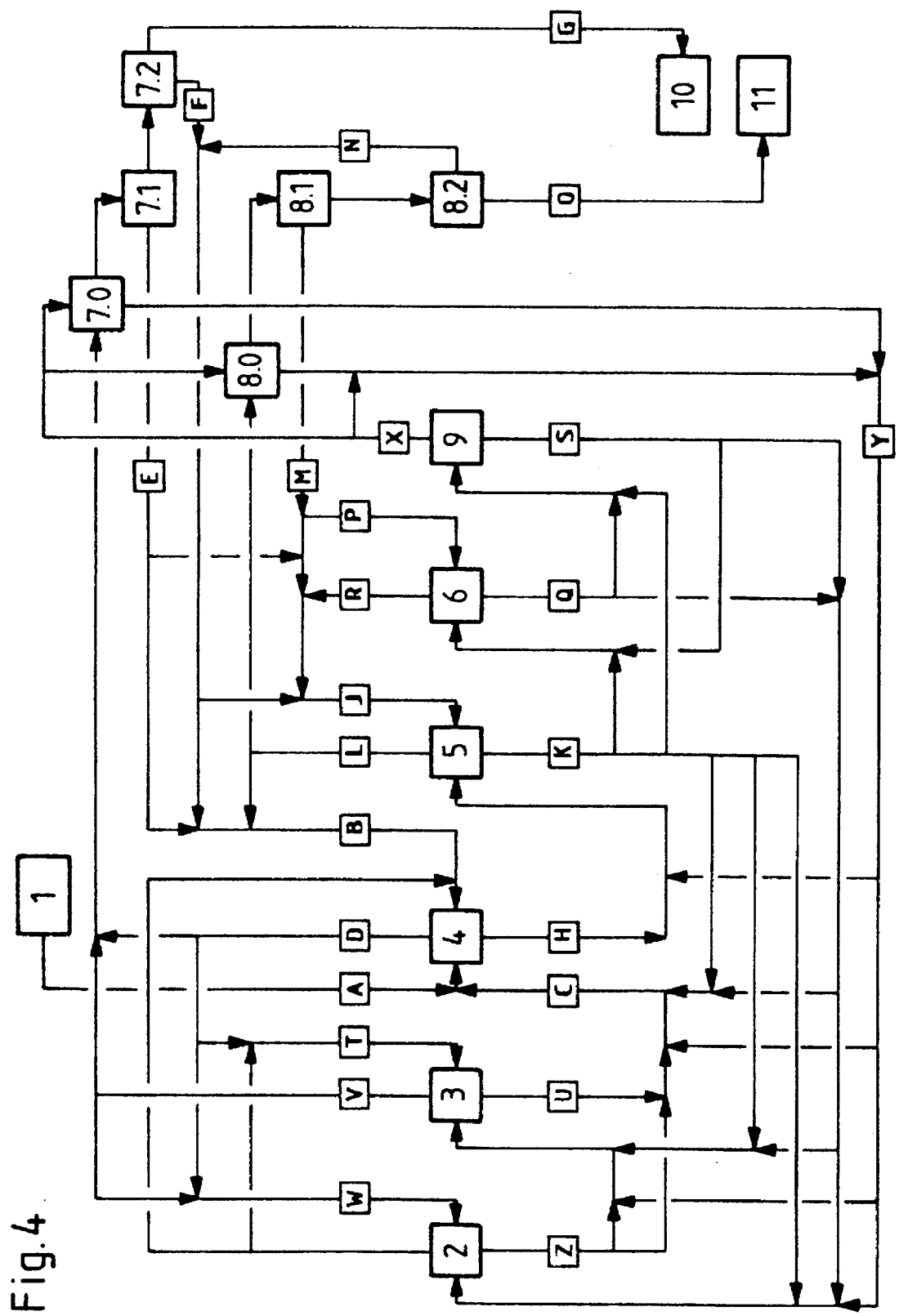

The process according to the invention may be carried out both with three (FIG. 1) and also with four (FIGS. 2 and 3) or five extraction stages (FIG. 4).

The flow diagrams of FIGS. 1–4 serve to explain further the process according to the invention, with the following references:

(1) a tank for the starting arylamine mixture
(2) an extraction stage (positioned upstream)
(3) an extraction stage (interposed)
(4) a (first) extraction stage
(5) a (penultimate) extraction stage
(6) a (final) extraction stage
(7) a working-up stage comprising
  (7.0) a washing stage,
  (7.1) a first distillation stage of a multi-stage distillation,
  (7.2) a final distillation stage of a multi-stage distillation,
(8) a further working-up stage comprising
  (8.0) a washing stage,
  (8.1) a first distillation stage of a further multi-stage distillation,
  (8.2) a final distillation stage of a further multi-stage distillation,
(9) a water evaporator
(10) a tank for a process product
(11) a tank for a further process product.

Reference letters A–Z designate the streams to which reference is made hereinbelow and in the Examples.

The extraction stage (2) positioned upstream is generally embodied as an extractor acting in multi-stage manner.

The extraction stage (3) which is optionally interposed likewise also comprises in the simplest instance a mixer-settler unit, however here too extraction units acting in multi-stage manner are preferably used.

The extraction stage (4) is in the simplest case a mixer-settler unit acting in single stage manner, however extraction units acting in multi-stage manner are preferably used.

The extraction stages (5) and (6) are generally embodied as extractors acting in multi-stage manner.

The working-up stages (7) and (8) serve to separate the polyamine fractions which arise as distillation residues and are isolated as process products (G) and (O) in the tanks (10) and (11), and to recover as distillates the hydrophobic solvent utilized and the auxiliary amine used.

The recovery of hydrophobic solvent and of auxiliary amine is generally associated with an extensive, optionally complete separation of the two components, and affords, on the one hand, in the form of distillate streams (E) and (M), hydrophobic solvent which is to a large extent impoverished at least as to auxiliary amine, optionally to a large extent liberated from auxiliary amine, and affords auxiliary amine which is to a large extent impoverished at least as to hydrophobic solvent, optionally to a large extent liberated from hydrophobic solvent, in the form of distillate streams (F) and (N), generally united in stream (S).

It has proved to be expedient to liberate the organic phases (D) and (D') and (L) and (L'), respectively, which are supplied to the distillation stages, from adhering traces of acid, by extracting with water, before their treatment by distillation in the washing stages (7.0) and (8.0) positioned upstream.

The actual working-up stage (7) generally comprises an at least two-stage multi-stage distillation whereof the first stage (7.1) delivers as the distillate (E) a hydrophobic solvent which by comparison with the intake product (D) or (D') is liberated from polyarylamine and is impoverished as to auxiliary amine, optionally liberated from auxiliary amine, and whereof the final stage (7.2) delivers as the distillate (F) an auxiliary amine which by comparison with (D) or (D') is liberated from polyarylamine and impoverished as to hydrophobic solvent, optionally liberated from hydrophobic solvent.

Additionally there arises in the final distillation stage (7.2), as the distillate bottoms (G), the first polyamine fraction of the starting mixture (A), which was contained in stream (D) or (D').

The working-up stage (8) also generally composes an at least two-stage multi-stage distillation whereof the first stage (8.1) delivers as the distillate (M) a hydrophobic solvent liberated, by comparison with the intake product (L) or (L'), from polyamine and impoverished as to auxiliary amine, optionally liberated from auxiliary amine, and whereof the final stage (8.2) delivers as the distillate (N) an auxiliary amine which, by comparison with (L) or (L'), is liberated from polyarylamine and impoverished as to hydrophobic solvent, optionally liberated from hydrophobic solvent.

The extensive, optionally complete, separation by distillation of hydrophobic solvent and auxiliary amine is preferred in carrying out the process according to the invention, and this applies in particular to the distillate fractions (M) and (E).

The distillation stage (9) is an apparatus with which water can be removed by distillation from the aqueous phase of the system or from a partial stream of the aqueous phase.

Such a step is fundamentally not a necessity for carrying out the process according to the invention, however because of the advantages those embodiments which include a water distillation stage (9) are preferred.

In the aqueous phase, which contains the acid, there is present in practical terms a closed circuit such that the stage (9) can be inserted fundamentally at any point in the latter circulation system. The position of stage (9) following the extraction stage (6) and before entry into the extraction stage (2), (3) or (4) is the most advantageous and hence the preferred embodiment.

The water volume (X) which is removed is, optionally after being split into partial streams and after being used variously, supplied again to the system at a suitable point in the form of the stream (Y) in its entirety or in partial streams, such that there results an enlarged and optionally branched closed-circuit aqueous system.

This latter also includes the washing stages (7.0) and/or (8.0). The latter are extraction stages acting in single or multi-stage manner operating on the countercurrent principle. In washing stage (7.0) the organic phase (D) or (D') is liberated from adhering traces of acid with a partial stream of (X), and in the washing stage (8.0) the same is effected with the organic phase (L) or (L') using another partial stream of (X).

The distillate (X), which is contaminated with hydrophobic solvent and auxiliary amine, is most suitable for the washing stages (7.0) and (8.0). The resulting washing waters generally exhibit a very much lower acid concentration than the actual acid circulation, such that they are able to be recycled without difficulty in the form of stream (Y) or partial streams thereof, optionally a distillate part volume of (X) can be guided past the washing stages to (Y) and used in order to select a different water content in the individual extraction stages.

Virtually quantitative circulation of the acid used enables costly acids such as, for example, methanesulphonic acid to be used, which in turn, having a lesser corrosive tendency, enable less costly materials to be used in the apparatus of the process according to the invention.

It has proved to be expedient to define the acid content of the aqueous phase, independently of the differing amine content which adjusts in the aqueous phase of a two-phase system, by way of what is known as a "molarity". The molarity is fixed as the theoretical concentration of amine which is 100% protonated (that is to say equal numbers of acid and amine equivalents) in a volume of aqueous phase, which is reduced by the proportion of non-protonated amine, in accordance with the formula:

$$\text{"Molarity"} = \frac{\text{Mol 100\%-protonated amine}}{\text{Vol. aqueous phase} - \text{vol. non-protonated amine}}$$

The molarity thus defined can assume values of up to 6 and, depending on the separation task which forms the basis for the embodiment in each case—in this instance, product-related—is varied in targeted manner within this range.

Even within one embodiment of the process according to the invention it is optionally advantageous to operate the individual process stages through which the aqueous phase passes, in particular the extraction stages (2) to (6), with differing molarity in the aqueous phase, by removing water from or supplying water to the aqueous phase between the individual stages.

This operational range has a practical upper limit, on the one hand as a result of the increasing tendency of the amine salts to crystallize as concentration increases, in particular in the case of high degrees of protonation, and on the other, as a result of the increasing mutual solubility of the phases in one another, in particular at low degrees of protonation.

According to a variant of the process according to the invention, the starting polyamine mixture (A) is fed from the supply tank (1) by mixing with the partial stream (C) and introducing the mixture into the extraction stage (4).

The stream (C) generally comprises water, a strong proton acid, auxiliary amine and optionally polyamine. The acid is present in the form of its salts dissolved in water, with auxiliary amine and optionally with polyamine. In (C) the sum of the amino groups of the auxiliary amine and optionally the polyamine is at all times present in a stoichiometric ratio or in excess, calculated on the acid.

The degree of protonation in (C) is generally from 40 to 100%, it is preferably around 60 to 100% for the aniline preferably used as the auxiliary amine.

The molarity of the stream (C), which is well-defined and is dimensioned and controlled within narrow limits for the respective embodiment of the process according to the invention, is varied in a targeted way within a broad range depending on the separation task which forms the basis for the embodiment in each case—in this instance product-related.

The aqueous phase (C) supplied to the extraction stage (4) of the process according to the invention generally has a molarity of up to 6, preferably between 0.5 and 4.0.

In the extraction stage (4) which is operated preferably in multi-stage manner, the stream (C) on which (A) impinges and the organic phase (B) are guided towards one another with intimate intermixing.

The organic phase (B) generally comprises, in addition to hydrophobic solvent, auxiliary amine and/or polyamine, the latter preferably having the composition of the second process part product (O).

When using an organic phase (B) without polyamine, there results in the aqueous phase (H) leaving the extraction stage (4) a polyamine fraction in which the relative enrichment of the components preferably contained in this phase can be increased and maximized in targeted manner at the expense of the polyamine concentration in the aqueous phase (H).

The effect of polyamine as a constituent of the organic phase (B) is that the phases (D) and (H) leaving the process stage (4) exhibit a higher polyamine concentration, which is hence more advantageous in energy terms for carrying out the process according to the invention, than is the case when an organic phase (B) without polyamine is used.

As a result of the, preferred, use of a polyamine having the composition of the second part product (O) as a constituent of the organic phase (B), the relative enrichment of the polyamine components preferably contained in the aqueous phase (H) leaving the separation phase (4), and hence of the second polyamine fraction (O), can also be varied and maximized at a higher and hence advantageous concentration level as a result of an equilibrium becoming established, with the separation effect being self-reinforcing.

In the simplest case, the stream (B) is formed from the stream (E) liberated from polyamine (G) and to a large extent impoverished as to auxiliary amine, which is obtained as the distillate in stage (7.1), optionally with the addition of a part volume of stream (S), comprising substantially auxiliary amine impoverished as to hydrophobic solvent and liberated from polyamine.

It is advantageous and preferred to incorporate first into the stream (J) which is used as the extraction agent in stage (5) at least part of the said stream (E) and optionally a corresponding volume of (S) and, after passage through the extraction stage (5), to remove from the resulting organic phase (L) and add to stream (B) a partial stream of (L) which is equivalent to a partial stream of (E) which is added by reference to the hydrophobic "solvent" content.

It is particularly preferred to add at least part of the said partial stream of (E) already to the organic phase (P) which is used as the extraction agent in the extraction stage (6) and to the extraction stage (5) as part of the resulting organic phase (R), and subsequently to stream (B) as a part volume of (L).

Optionally, according to a less generally applicable form of use, the feeding of hydrophobic solvent and auxiliary amine from other sources may be dispensed with completely when forming stream (B), such that the organic phase (B) comprises exclusively a part volume of (L). This embodiment of the process according to the invention is particularly advantageous in terms of separation efficiency and energy balance and is hence particularly preferred when it can be applied.

Optionally, in a less generally applicable embodiment, the total volume of streams (E) and (F) is added to the stream (J) and is first used as the extraction agent in extraction stage (5) such that stream (B) is formed exclusively from a part volume of stream (L) leaving the extraction stage (5).

The aromatic amine content of the organic phase (B) is generally 25–60%, depending on the separation task.

In the extraction stage (4) which is preferably operated in multi-stage manner, the organic phase (B) and the mixture of starting polyamine mixture (A) and aqueous phase (C) are guided towards one another with intimate intermixing. In this procedure, there generally takes place a partial transfer of polyamine into the organic phase, optionally in exchange for auxiliary amine in the opposite direction.

The starting polyamine (A) introduced together with the aqueous phase (C) into the extractor (4) is distributed between the aqueous phase (H) leaving the extractor and the organic phase (D) leaving the extractor (quantitative fractionation).

In terms of volume, the individual components of the starting polyamine mixture are distributed between the resulting aqueous phase (H) and the resulting organic phase (D) with a selectivity which is surprisingly high, under the conditions of the process according to the invention, such that the resulting product fractions exhibit a different composition which under some circumstances deviates markedly from that of the starting polyamine mixture (qualitative fractionation).

For example, taking as a basis the aniline/formaldehyde condensation products which are preferably utilized, it has been found that in the case of a polyamine component contained in the starting mixture in two or more isomeric forms, generally the ortho-isomeric form or forms thereof in the organic phase (D) leaving the separation stage (4) is/are relatively enriched; for example, 2,4'-diaminodiphenylmethane relative to 4,4'-diaminodiphenylmethane. The resulting aqueous phase (H) is, vice versa, relatively impoverished as to the 2,4'-isomer, whereas the 4,4'-isomer is relatively enriched.

If a number of "ortho-isomers" are present in the starting polyamine, for example 2,2'- and 2,4'-diaminodiphenylmethane, then the "ortho-richer" 2,2'-isomer in the organic phase (D) is more strongly enriched than the "ortho-poorer" 2,4'-isomer, which latter is, for its part, relatively enriched as compared with the "even more ortho-poor" 4,4'-isomer.

The enrichment and impoverishment effect first found with the aniline/formaldehyde condensation products of the diaminodiphenylmethane series has been linked in a purely empirical-descriptive way with the criterion of ortho- and para-substitution. The characterization of the process products which is derived from this as "ortho-rich" and "ortho-poor" is here relative and has been expressed by the concept of the "degree of ortho-substitution".

Here, the ratio of the amino groups in the ortho position proportional to the methylene groups to the total number of all the amino groups as a proportion is defined as the "degree of ortho-substitution". This concept can cover virtually all the isomer separations in the polyamines prepared from arylamines, including substituted arylamines, with carbonyl compounds in an aqueous acid medium.

The same enrichment and impoverishment effect— ordered according to the degree of ortho-substitution—has now surprisingly also been found in respect of the well characterized and analytically identifiable isomeric tri-nuclear compounds from aniline/formaldehyde condensation.

The same applies to separation of the isomers of condensation products of formaldehyde with aniline and diaminoaryl compounds such as phenylenediamine or alkyl-substituted phenylenediamines.

The polyamine mixtures mentioned thus far exhibit, by virtue of their method of preparation, amino groups which are virtually only in the ortho and/or para position to methylene groups. In this case within a group of isomeric compounds it is generally those having the higher degree of ortho-substitution which are enriched during fractionation in the organic phase (D), as compared with the isomers having a lower degree of ortho-substitution.

Polyamine mixtures in particular of the diphenylmethane series, including the respective higher-nuclear homologues, which are manufactured by other processes, for example by the nitration of diphenylmethane or methyldiphenyl-methanes followed by reduction, also exhibit other amino group-methylene group relations, in addition to amino groups in the ortho and para positions, by virtue of their method of preparation. The process according to the invention is equally effective for these polyamine mixtures.

For example, nitration and subsequent reduction can be used to prepare from a mixture of 2- and 4-methyldiphenylmethane a polyamine mixture which principally constitutes an isomer mixture of

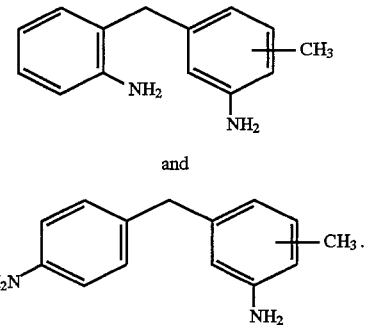

Fractionation of such mixtures with the aid of the process according to the invention enriches the 3,2'-amino isomers in the organic phase (D) compared with the 3,4'-amino isomers.

Not all the isomers in these polyamine mixtures still fit the criterion of "ortho-rich" and "ortho-poor" or of the degree of ortho-substitution, which should therefore be applied by analogy, by classifying the isomers into those having a smaller (=ortho-) and those having a greater (=para-) spatial distance between the—generally to be found on different six-membered rings—amino groups and the methylene bridge or between the amino groups themselves, in place of the terms "in the ortho position" and "in the para position".

A further class of aromatic polyamine mixtures which can be fractionated very effectively with the aid of the process according to the invention is constituted by the polyamines of triphenylmethane and the higher-nuclear homologues of triphenyl-methane, preferably benzyl homologues, such as are prepared, for example, by the nitration and reduction of the corresponding hydrocarbon mixtures.

When fractionating technical grade polyamine mixtures of the last-mentioned class of substances:

I. co-condensation products of mono- and diaminoaryl compounds with formaldehyde or general carbonyl compounds, II. polyamine mixtures from processes involving the nitration and subsequent reduction of diphenylmethane and preferably substituted, in particular alkyl-substituted, diphenylmethanes and the respective homologues and III. polyamine mixtures from processes involving the nitration and subsequent reduction of triphenylmethane and preferably substituted, in particular alkyl-substituted, triphenylmethanes and the respective higher-nuclear benzyl homologues a further surprising selectivity was found in addition to the pure isomer separation.

Polyamine mixtures of the named substance classes I to III contain or may contain components in which one aryl ring carries per molecule more than one, generally two, amino groups. These components can be the preferred constituents of the polyamine mixture, without being necessarily, by virtue of the process, the principal products in volume terms.

In order better to characterize such components, the concept "degree of amino substitution" is used, characterizing in the first instance the number of amino groups of a component in relation to the number of aryl rings.

In the case of aniline and condensation products thereof with formaldehyde, this expression is always 1.0, and for phenylenediamine and condensation products thereof always 2.0. In the case of pure co-condensates the value for the diphenylmethane isomers is 1.5 and for the higher-nuclear homologues is between >1.0 and <2.0. Likewise the values are between 1.0 and 2.0 if the concept "degree of amino substitution" is used in random manner to characterize polyamine mixtures.

It has now been found when fractionating polyamine mixtures having components having a degree of amino substitution of >1.0 that the components having a higher degree of amino substitution are relatively enriched in the aqueous phase (H) resulting in the actual separation step, in fact the more markedly the greater the degree of amino substitution.

Independently of this, separation according to the degree of ortho-substitution is also effective here. Consequently, the process according to the invention opens up for this substance class, too, new ways of decoupling the manufactured form of the raw materials (amine stage) and the used form of the end products (isocyanate stage) by fractionation and/or enrichment in the amine stage and separate further processing of the fractions, such that it becomes easier, or even for the first time possible, to optimize both stages separately up to and including obtaining completely new isocyanate mixtures, where hitherto suitable processes and methods have been either lacking or largely impracticable.

These achievements are complemented by a further criterion of selectivity which was found when fractionating technical grade polyamine mixtures, in particular those having higher-nuclear homologues, which relates to the "nuclearity" of the polyamine mixtures.

The term "nuclearity" expresses primarily the number of aryl units in a component of an aromatic polyamine mixture. In the broader sense, the concept of nuclearity is used in order to express as a random value a nuclearity of the total mixture where a polyamine mixture comprises numerous components each having its own precise nuclearity.

Particularly surprisingly, it has now been found when fractionating polyamine mixtures having higher-nuclear constituents, in particular when fractionating technical grade mixtures of aniline formaldehyde condensates, that the higher-nuclear components can, in targeted manner, be both relatively enriched and also relatively impoverished in the organic phase leaving the fractionation stage, in dependence on the molarity of the aqueous phase in the extraction stage (4).

A high molarity of the aqueous phase in (4) within the indicated molarity range leads to a relative impoverishment of higher-nuclear components in the organic phase (D) and accordingly to a relative enrichment in the aqueous phase (H).

A low molarity of the aqueous phase in (4) within the indicated molarity range leads to a relative enrichment of higher-nuclear components in the organic phase (D).

The surprising finding can be expanded and rendered more specific in that the relative enrichment and impoverishment also take place within the higher-nuclear homologues among themselves. If, for example, in an technical grade mixture of diaminodiphenylmethane, the trinuclear components in the one fraction are enriched or impoverished relative to the binuclear components, then an enrichment or impoverishment of tetranuclear components relative to trinuclear components, i.e. an even more marked relative enrichment or impoverishment, is found, and so forth in the case of pentanuclear components relative to tetranuclear components, etc.

This and the isomer separation which always takes place in the sense of a relative reinforcement of the "degree of ortho-substitution" in the organic phase (D), and the possibility of repeating with individual product fractions the separation according to the invention, optionally with changed process parameters, gives rise to numerous possibilities for gaining access, by way of the process according to the invention, to less readily accessible polyamines, and hence polyisocyanates, or to those which, not having hitherto been accessible according to the prior art, would be completely novel, starting from known and readily accessible polyamine mixtures. This applies particularly to products of the diamino- and diisocyanatodiphenylmethane series and quite particularly to polyamine mixtures and polyisocyanate mixtures having an extremely high proportion of higher-nuclear components.

The enrichment and impoverishment are generally more effective as the degree of protonation in the aqueous phase of the separation stage increases.

Furthermore, the process according to the invention also proves to be generally effective with other polyamines of similar structure. Thus, for example, the polyamine mixtures already mentioned which are obtained by the nitration of di- and polyarylmethanes followed by reduction may also contain monoaminopolyarylmethane compounds or components in which one or more methylene groups have been converted by side reactions into keto- and/or hydroxymethylene groups and thus into undesirable by-products.

Numerous incompletely rearranged intermediate compounds and by-products can occur when condensing arylamines with carbonyl compounds. During fractionation of the polyamine mixtures which contain these compounds, the majority are generally subject to an enrichment in one of the resulting fractions, such that the effect can be used for separation and fractionation.

Such products may optionally be enriched or impoverished in this way or they may be fractionated in their own right as intentionally prepared polyamine mixtures, such as for example polyaminobenzophenones or aminobenzyl arylamine mixtures.

The organic phase (D) leaving the extraction stage (4) still contains, inter alia, small quantities of acid, generally and depending on the process parameters in the extraction stage (4) between 0.01 and 0.5 wt. %, which are advantageously removed before the stream (D) is worked up by distillation. In the simplest case this takes places by neutralization with excess dilute aqueous bases, for example dilute sodium hydroxide. However, the acid or amine salts thereof are preferably washed out of the organic phase with water such that optionally only traces which remain are removed by contact with dilute sodium hydroxide or with the aid of an ion exchanger.

The washing water used is removed from the aqueous acid circulation by inserting a water evaporator and after passing through the washing stage(s) is added again, together with the acid, to the aqueous acid circulation, at a point which is suitable in terms of the process.

The organic phase (D) or (D') is transferred, optionally after passing through the acid washing stage (7.0), into the at least two-stage distillation stage (7.1), (7.2).

In the first distillation stage (7.1) a distillate (E) is separated which includes the majority, preferably almost the entire volume, of the hydrophobic solvent contained in (D) or (D'), optionally in addition to part of the auxiliary amine contained therein.

In the final distillation stage (7.2) the remaining auxiliary amine, optionally in addition to the residual volume of hydrophobic solvent, is separated as the distillate (F) from the first part product (G) arising as the distillation bottoms and collected in the process product tank (10).

The corresponding second process product is to be found in the aqueous phase (H) leaving the extraction stage (4).

In an extraction stage (5) acting in multi-stage manner, operated preferably at 80° to 100° C., the second part product is extracted from the aqueous phase (H) in exchange for auxiliary amine, optionally after the addition of water to reduce the molarity and optionally after the addition of auxiliary amine to reduce the degree of protonation, and in the course thereof is transferred into the organic phase (L).

The molarity of the aqueous phase used in (5) is preferably <2.5. The degree of protonation of the aqueous phase used in (5) is preferably <60%.

A mixture of hydrophobic solvent and auxiliary amine, which is formed substantially from the organic phase (R) leaving the subsequent extraction stage (6), optionally distillate (M), optionally a part volume of (E) and generally a part volume of stream (S), serves as the extraction agent (J).

The ratio by weight of auxiliary amine to solvent in (J) is generally between 0.5:1 and 3:1, preferably between 1:1 and 2:1. The ratio by weight of extraction agent (J) to aqueous phase is generally between 0.3:1 and 3:1, preferably between 0.7:1 and 2:1.

The organic phase (L) or (L') resulting in (5) is supplied to the distillation stages (8.1) and (8.2), optionally after passing through the washing stage (8.0) and/or optionally after removal of traces of acid with dilute sodium hydroxide.

In the distillation stage (8.1), (8.2) there takes place the separation by distillation of the distillation residue (O) which is collected in the process product tank (11) as the second part product.

The working-up stage (8) generally comprises an at least two-stage multi-stage distillation (8.1), (8.2) in stage (8.1) whereof there is obtained as the distillate (M) a hydrophobic solvent which is liberated from polyamine and is markedly impoverished as to auxiliary amine, compared with the intake product (L) or (L').

The auxiliary amine content in (M) is generally <30%, preferably <20%; a hydrophobic solvent liberated from auxiliary amine is optionally obtained in (8.1) as a distillate. At least part of the distillate (M) is utilized, optionally also after the addition of a part volume of (E) from the distillation stage (7.1), in the extraction stage (6) as the organic phase (P) for the counter-current extraction of at least a part volume of the aqueous phase (K) resulting in the extraction stage (5), at least part of which is supplied to the extraction stage (6) directly and/or indirectly by way of an interposed distillation stage (9).

During the extraction procedure which takes place in the extraction stage (6) auxiliary amine and optionally polyamine which is still present are removed from the aqueous phase such that the resulting aqueous phase (Q) exhibits at all times a higher degree of protonation than the aqueous phase (K) from the extraction stage (5).

The degree of protonation of (Q) is generally >50%, preferably 60%, and may be up to 100% when pure hydrophobic solvent is used as (P).

The recycled aqueous phase (C) exhibits a higher degree of protonation than the aqueous phase (K) leaving the extraction stage (5). In the case of degrees of protonation which although higher than that of (K) are <100%, this can be achieved in that either the entire aqueous phase passes through the extraction stage (6) or only a corresponding part volume which, optionally having a degree of protonation of 100%, affords the elevated—compared with (K)—degree of protonation of (C), as a result of mixing with the remainder.

A degree of protonation of virtually 100% in the aqueous phase (C) can be achieved only if the entire aqueous phase passes at least once by way of the extraction stage (6) and in so doing is extracted with virtually pure hydrophobic solvent.

Because the aqueous phase (C) according to the invention exhibits a degree of protonation greater than the degree of protonation preferred in the aqueous input phase to the extraction stage (5), it may be necessary and advantageous to adjust such a preferred degree of protonation in the aqueous input phase to the extraction stage (5) by the addition at a suitable point of auxiliary amine and/or polyamine.

Suitable points for amine supply are the aqueous phase immediately before entering the extraction stage (5) with use of auxiliary amine, or at a point positioned upstream, preferably before the aqueous phase enters the extraction stage (3), for example by direct addition or by way of an extraction stage (2) positioned upstream.

A further important parameter of the returned and recycled aqueous phase (C) is molarity. According to the invention, the molarity of (C) may be varied over a broad range in dependence on the respective separation task.

Fundamentally, the aqueous phase (H) resulting in process stage (4) may be supplied directly to the extraction stage (5). However, because the upper molarity range of the extraction stage (4), a range which is far preferred for certain separation tasks, exceeds the preferred molarity range of the extraction stage (5), it is a preferred embodiment of the process according to the invention to decouple the molarities in the different extraction stages by optionally removing water by distillation from the closed circuit of the aqueous phase, at a suitable point, and adding it again at a different suitable point.

With the aid of a water distillation stage (9) water is removed from the aqueous phase which contains the acid, or from a partial stream of the aqueous phase, preferably after leaving the extraction stage (5) and before recycling at the beginning of the process, and is added again, in total (Y) or in part quantities, at one or more points, at the latest before the aqueous phase enters the extraction stage (5).

It is irrelevant to carrying out the process according to the invention whether the removal of water in (9) takes place before or after passing through the extraction stage (6).

The water (X) removed in (9) may be used simultaneously to operate the washing stages (7.0) and/or (8.0). The water volume (X) may also be removed predominantly or exclusively to operate the washing stages (7.0) and/or (8.0). This first variant on the process according to the invention affords the opportunity for considerable separation efficiencies in the fractionation of polyamine mixtures and enables numerous separation problems to be resolved in a satisfactory way.

In particular in the second polyamine fraction (O) the relative enrichment of the components preferably contained in this fraction can be varied and maximized in targeted manner.

The proportion of these components remaining in the first polyamine fraction (G) cannot, however, be minimized in the same way according to this first variant, but may be impoverished relatively in variable manner only up to a content whose lower limit depends on that distribution equilibrium of the polyamine components of (A), which is characteristic of the respective process parameters, between the aqueous phase on entering the extractor (4) and the organic phase (D) on leaving the extractor (4).

A second variant of the process according to the invention is more advantageous and is a preferred embodiment; in this, in the first polyamine fraction (G) too, it is additionally possible to increase considerably and to vary in targeted manner the relative enrichment of the components preferably contained in this fraction, in that the organic phase (D) which arises in the extraction stage (4) is extracted at least in part in an extraction stage (3) which is interposed from the point of view of phase (D), with an aqueous phase which in the present case of variant 2 comprises substantially at least a part volume of stream (C).

For formal reasons the organic phase supplied to the extraction stage (3) is designated stream (T) even if it optionally matches stream (D) at least in composition, but preferably also in volume, as embodied by way of example in the present case.

Carrying out the extraction stage (3) even only in single-stage manner, for example as a mixer-settler unit, results in a markedly further relative enrichment in the resulting organic phase (V), dependent on the type and in particular the volume of the aqueous phase utilized, of those components already enriched in (D) as compared with starting polyamine (A), combined with a reduction in the polyamine content of the organic phase (V). Preferably, however, the interposed extraction stage (3) is also embodied as an extractor acting in multi-stage manner and operated in countercurrent, this being more effective, The aqueous phase (U) arising in the extraction stage (3) contains the corresponding other fraction of the polyamine introduced with stream (T), in which fraction the components enriched in (V) are correspondingly impoverished. The extent of relative impoverishment which can be achieved, that is to say the composition of the polyamine contained in (U), is controlled under the respective process conditions of the extraction stage (3) acting in multi-stage manner, by the qualitative and quantitative distribution equilibrium between the organic phase (T) supplied and the aqueous phase (U) discharged.

The molarity of the aqueous phase in the extraction stage (3) is, depending on the separation task, higher than or as high as or lower than the molarity in the extraction stage (4) which is positioned downstream from the point of view of the aqueous phase, and is regulated by the addition or removal of water at a suitable point.

The aqueous phase (U) resulting in stage (3) is supplied optionally after the addition of water together with the optionally present residue of (C) to the extraction stage (4).

The organic phase (V) resulting in stage (3) is supplied together with the optionally present residue of (D) to the working-up stage (7) in order to obtain the polyamine fraction (G).

With the second variant on the process according to the invention the relative enrichment can be varied and maximized in targeted manner in both resulting polyamine fractions. In addition to this great versatility and power in terms of quality, the second process variant also affords an embodiment which is favorable as to energy at least for the second polyamine fraction (O).

The energy consumption associated with obtaining the first polyamine fraction (G), on the other hand, increases in relative terms more markedly the lower the quantitative proportion of (G), calculated on polyamine mixture (A) utilized, because the remaining polyamine (G) content in the organic phase (D) and/or (V) which are/is to be worked up by distillation becomes correspondingly ever smaller.

The effect carries particular weight when the components separated with (G) are contained only at a low concentration in the starting mixture (A) and/or are relatively highly enriched in the fraction (G), for example in the separation according to the invention of polyamine mixtures of the diphenylmethane series.

An embodiment which is improved in this respect is represented by the third variant on the process according to the invention. Proceeding on the basis of the first variant, this is broadened in that the organic phase (D) leaving the process stage (4) is divided into a partial stream (D') which continues to be supplied to the working-up stage (7) with the aim of obtaining the polyamine fraction (G), and a second partial stream which is supplied to an extraction stage (2) positioned upstream.

For formal reasons the organic phase supplied to the extraction stage (2) positioned upstream is designated stream (W) even when it optionally matches stream (D) in composition, as embodied by way of example in the present case.

The extraction stage (2) is generally an extractor acting in multi-stage manner and operated in countercurrent, in which the organic phase (W) supplied is extracted with at least a part volume of the aqueous phase (C) which is available for recycling.

The stream (W) supplied to the extractor (2) is here dimensioned such that when it is reacted with stream (C) there takes place as extensive a transfer as possible, preferably virtually quantitative, of the polyamines contained in the organic phase (W) into the aqueous phase (Z) leaving the extractor (2).

An elevated molarity in the aqueous phase utilized in stage (2), resulting from process stage (9) of the process according to the invention, favors and facilitates the transfer of polyamine from the organic phase (W) into the aqueous phase (Z).

An elevated degree of protonation of the aqueous phase utilized in stage (2), resulting from process stage (6) of the process according to the invention, likewise favors and facilitates the transfer of polyamine from the organic phase (W) into the aqueous phase (Z).

The residual polyamine content of the organic phase leaving the process stage (2) is generally around <5 wt. %, preferably around <1 wt. %.

For the rest, the permitted maximum amine, and in particular polyamine, content is determined by the quality demands of the process products, set by the respective separation task, that is to say the quality of separation, in the case of variant 3 in particular the demands made of the process part product (O). Maintenance of the polyamine content which is relevant to the quality of (O) is controlled within the framework of the technical factors by way of dimensioning the part stream (W), with exhaustion of the available aqueous phase.

Here it is useful to the process and in particular to extraction stage (2) that the aqueous phase available for utilization in stage (2) (stream C) is greater the greater the proportion of the second polyamine fraction (O) and the smaller, consequently, the proportion of the first polyamine fraction (G). A small polyamine fraction (G) generally signifies a low polyamine concentration in the organic phase (D) and a high energy consumption for working up such a phase.

It is possible by means of variant 3 according to the invention, as compared with variant 1, to reduce in particular the energy consumption for isolating the first polyamine fraction (G).

The contribution which process stage (2) within the framework of variant 3 makes towards improving the process according to the invention is that the working-up (6) by distillation to obtain the first polyamine fraction (G) affords, instead of the total stream (D) having a polyamine concentration which is relatively low and hence unfavorable in energy terms, only a partial stream (D') having a concentration which is correspondingly higher and hence more favorable in energy terms (quantitative enrichment) results, while an organic phase which can be used at a suitable point as an extraction agent is obtained without distillation from the other partial stream of (D).

The organic phase leaving process stage (2), which is largely liberated from polyamine, is supplied to the extraction stage (4) and utilized as an extraction agent, generally by mixing with stream (B) and addition to the, from the point of view of the organic phase (B), first stage of the extractor (4).

In dependence on a residual polyamine content which is optionally present and taking account of the quality of the second polyamine fraction (O), the addition of the organic phase obtained in (2) is effected optionally to an extraction stage (4) which is, from the point of view of the organic phase (B), later, optionally to the final stage of the extraction stage (4) which operates in multi-stage manner.

The aqueous phase leaving the process stage (2) still contains, in addition to the acid which is present in the form of its ammonium salts, auxiliary amine and polyamine, the latter having a composition which largely corresponds to the polyamine in the supplied organic phase (W).

In the case of variant 3 of the process according to the invention, the stream is supplied directly to the process stage (4), optionally after the addition of water from stream (Y) and/or of further aqueous phase from stream (C).

Because the polyamine fraction contained in the aqueous phase generally exhibits a higher relative (qualitative) enrichment in terms of the first polyamine fraction (G), by reference to the starting polyamine (A), the result for the aqueous phase supplied to the extraction stage (4) after the addition of starting polyamine (A) is a mixed polyamine which is "enriched" by comparison with the starting polyamine (A) in dependence on the quantitative ratio. As a result of the distribution equilibrium between supplied aqueous and resulting organic phase (D), the result for variant 3 is also a limited qualitative enrichment effect for the first polyamine fraction (G).

In a further variant 4 of the process according to the invention, the technical measures of the preceding variant are brought together and combined.

In the simplest case the extraction stages (2) and (3) are added and each independently carried out in the manner described with a partial stream of (C) and a partial stream of (D), which is in this case divided into 3 partial streams.

It is more advantageous to utilize as the organic phase (W) in extraction stage (2) a partial stream of the qualitatively highly enriched, quantitatively less concentrated polyamine fraction contained in the stream (V).

The variant 4 is preferably carried out such that as the organic phase (W) a partial stream of (D) and/or preferably a partial stream of (V) is utilized in the extraction stage (2), and at least part, preferably all, of the aqueous phase (Z) resulting in stage (2) is supplied to the extraction stage (3) and is utilized in (3) optionally with the addition of further aqueous phase from stream (C) and optionally of auxiliary amine. In so doing, the organic phase (T) with its content of polyamine enriched in the same way is guided towards this with intimate intermixing in several stages, optionally the organic phase (T) is strengthened by the addition to (T) of a partial stream of the organic phase resulting in the extraction stage (2).

The outcome of this measure is a further increase in the qualitative enrichment effect in the organic phase (V) resulting in (3). In quantitative terms this result can be achieved in the phases which result in (3), in particular in the organic phase (V), by dimensioning and dividing the streams at a polyamine content which is relatively high and hence favorable in energy terms.

The back-coupling of the enrichment effect in (V) by way of stream (W) as a partial stream of (V) and by way of the aqueous phase (Z) here has a self-reinforcing effect.

By embodying and re-positioning the extraction stages (2) to (4) in variant (4) with process criteria such as disproportionation in place of fractionated extraction in stage (3), with self-reinforcement by repositioning with extraction stage (2), and recovery of extraction agent in stage (2) without distillation for utilization in process stage (4) and optionally in (3), there results maximum qualitative separation efficiency which, combined with varying the molarity of the aqueous phases in stages (2) to (4), leads to a wide range of applications for the process according to the invention.

The invention is further illustrated but is not intended to be limited by the following examples in which all parts and percentages are by weight unless otherwise specified.

EXAMPLE

Starting polyamine mixture (A) (1.600 kg/h) is mixed with stream (C) (5.050 kg/h) which comprises substantially polyamine mixture, aniline, hydrochloric acid and water.

The resulting aqueous phase (streams A+C) has the following average composition:

| Stream (A) + (C) (6.650 kg/h) | 24.7% polyarylamine 15.1% aniline 6.0% hydrochloric acid 54.2% water |
|---|---| and in an extractor (4) which acts in multi-stage manner at 90° C. is guided towards the organic stream (B) which has the following composition:

| Stream (B) (2.700 kg/h) | 37.3% aniline 62.1% xylene ≦0.6% water. |
|---|---|

The resulting organic phase (stream D) leaving the extraction stage (4) has the following average composition:

| Stream (D) (3.009 kg/h) | 23.4% polyarylamine 19.2% aniline 55.7% xylene ≦0.1% hydrochloric acid ≦1.6% water. |
|---|---|

Stream (D) is washed in the washing stage (7.0) with water (0.300 kg/h) as part of stream (X). The washing water is supplied by way of stream (Y) to the aqueous stream (H).

For safety, the washed stream (D) is washed with dilute sodium hydroxide. The aqueous phase is disposed of as effluent.

Stream (D) which is washed and liberated from acid esters is liberated from xylene and some of the aniline in a first distillation stage (7.1). Some of the water is separated mechanically from the distillate stream (E) and is added to stream (X).

In the second distillation stage (7.2), the remaining aniline (stream F) is separated from the bottom phase of (7.1). The distillation bottoms remaining from stage (7.2) are constituted by a polyamine mixture which is collected in the tank (10) at a rate of 0.704 kg/h as stream (G).

The distillate streams (E) and (F) together with a part volume of 0.430 kg/h from stream (N) form the stream (B).

The aqueous phase (H) leaving the extraction stage (4) has the following average composition:

| Stream (H) (6.341 kg/h) | 14.8% polyarylamine 22.6% aniline 6.2% hydrochloric acid 56.4% water. |
|---|---|

After admixing stream (Y) (0.908 kg/h) the resulting aqueous phase is extracted in countercurrent with an organic phase (stream J) in an extractor (5) acting in multi-stage manner at 90° C.

| Stream (J) (4.200 kg/h) | 52.1% aniline 47.3% xylene ≦0.6% water |
|---|---|

The organic phase (stream L) thus resulting and leaving the extraction stage (5) has the following composition:

| Stream (L) (4.940 kg/h) | 18.1% polyarylamine 39.0% aniline 40.2% xylene ≦0.1% hydrochloric acid ≦1.6% water. |
|---|---|

Stream (L) is washed in the washing stage (8.0) with water (0.600 kg/h) as part of stream (X). The washing water is supplied to the aqueous stream (H) by way of stream (Y).

For safety, the washed stream (L) is washed with dilute sodium hydroxide. The aqueous phase is disposed of as effluent.

The stream (L) which is washed and liberated from acid esters is then separated in a first distillation stage (8.1) into a first distillate fraction (M) which comprises virtually xylene with an aniline content of ≦1% [Stream (M) (2.033 kg/h)], and a distillation bottom product which in a second distillation step is separated into a second distillate fraction (N) which comprises virtually aniline [Stream (N) (1.953 kg/h) and a distillation residue (O) comprising polyamine [Stream (O) (0.896 kg/h)].

The polyamine fraction (O) is collected in the tank (11) as a second part product.

The aqueous phase (K) leaving the extractor (5) has the following average composition

| Stream (K) (6.509 kg/h) | 0.6% polyarylamine 25.3% aniline 6.1% hydrochloric acid 68.0% water |
|---|---| and is guided towards an organic phase (P) in a further extractor (6) acting in multi-stage manner at 90° C. (P) is in the present case identical as to volume and composition to the first distillate fraction (M) from distillation stage (8.1).

In this procedure the stream (R) results as the organic phase

| Stream (R) (2.677 kg/h) | ≦0.2% polyarylamine 24.8% aniline 74.2% xylene <1.0% water. |
|---|---|

The stream (J) is formed from stream (R) by admixing a partial stream of (N) (1,523 kg/h).

The aqueous phase (Q) resulting in (6) has the following average composition:

| Stream (Q) (5.865 kg/h) | 0.6% polyarylamine 17.1% aniline 6.8% hydrochloric acid 75.5% water. |
|---|---|

In a subsequent distillation stage (9) water is removed from the aqueous phase (Q) by distillation in the form of the stream (X) [Stream (X) (0.815 kg/h)].

The water distilled off in (9) together with the water separated mechanically in the distillation stages (7.1) and (8.1) is used to wash the organic phase (D) in (7.0) and the organic phase (L) in (8.0). The resulting washing waters are combined in stream (Y) and are added to the aqueous stream (H) before the latter enters the extraction stage (5).

The aqueous phase (S) resulting in the distillation stage (9) is supplied to the extraction stage (4) and in the present case is identical as to volume and composition to the aqueous stream (C) used there.

| Polyarylamine | A | G | N |
|---|---|---|---|
| 2,2'-diaminodiphenylmethane | 0.50 | 1.15 | — |
| 2,4'-diaminodiphenylmethane | 11.60 | 25.45 | 0.70 |
| 4,4'-diaminodiphenylmethane | 51.50 | 35.50 | 64.10 |
| N-methyl-4,4'-diaminodiphenylmethane | 0.40 | 0.90 | <0.10 |
| Σ-diaminodiphenylmethane | 64.00 | 63.00 | 64.80 |
| Σ-polynuclear polyamines | 36.00 | 37.00 | 35.20 |
| Quantitative distribution | 100% | 44.0% | 56.0% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the fractionation and purification of aromatic polyamine mixtures comprising:
a) mixing the polyamine starting mixture in a first extraction stage with a two-phase system comprising
  (i) a hydrophobic solvent phase which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and
  (ii) an aqueous phase consisting essentially of water, a strong acid and auxiliary amine present at least in part in the salt form, and optionally polyamines present at least in part in the salt form, with said first extraction stage operating on the countercurrent principle, and wherein said polyamine starting mixture is introduced into said first extraction stage with said aqueous phase, with a first aqueous phase and a first organic phase exiting said first extraction stage, b) distilling said first organic phase in a first multi-stage distillation into
  i) a first, recycled fraction consisting essentially of hydrophobic solvent and optionally auxiliary amine,
  ii) a second, recycled fraction consisting essentially of auxiliary amine and optionally hydrophobic solvent, and
  iii) a distillation residue consisting essentially of a first polyamine fraction, c) extracting said first aqueous phase in a second extraction stage with a solvent phase consisting essentially of hydrophobic solvent and auxiliary amine, said second extraction stage operating on the countercurrent principle, with
  i) a second aqueous phase, said second aqueous phase being reduced in polyamine content and ii) a second organic phase exiting said second extraction stage, d) separating at least a portion of said second organic phase in a second multi-stage distillation into
  i) a first fraction consisting essentially of hydrophobic solvent and optionally proportions of auxiliary amine,
  ii) a second fraction consisting essentially of auxiliary amine and optionally proportions of hydrophobic solvent, and
  iii) a distillation residue consisting essentially of a second polyamine fraction, e) extracting at least a portion of said second aqueous phase in a third extraction stage with an organic phase consisting essentially of hydrophobic solvent and optionally auxiliary amine, said third extraction stage operating on the countercurrent principle, with i) a third aqueous phase, said third aqueous phase being reduced in amine content and ii) a third organic phase exiting said third extraction stage, f) recycling said third aqueous phase as at least a portion of said aqueous phase, and g) recycling said third organic phase to said second extraction stage as at least a portion of said solvent phase.

2. Process for the fractionation and purification of aromatic polyamine mixtures characterized in that a) the polyamine starting mixture (A) is distributed, with intermixing of the phases, in a two-phase system comprising (i) a hydrophobic solvent phase (B) which comprises substantially hydrophobic solvent and optionally an aromatic auxiliary amine which is virtually insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) comprising substantially water, a strong acid and auxiliary amine present at least in part in the salt form, and optionally polyamines present at least in part in the salt form, with the use as an aid of an extraction stage (4) operating on the countercurrent principle, in that the starting polyamine mixture is introduced into the extraction stage (4) with the aqueous phase, and the organic phase (D) leaving the extraction stage (4) is, b) optionally at least in part by way of an interposed extraction stage (3) and/or c) optionally with separation of a partial stream upstream or downstream of the extraction stage (3) which is optionally passed through and return of the separated partial stream to the extraction stage (4) by way of an extraction stage (2) positioned upstream, d) separated in a multi-stage distillation (7.1), (7.2) into a first, recycled fraction (E) comprising substantially hydrophobic solvent and optionally auxiliary amine, a second fraction (F) comprising substantially auxiliary amine and optionally hydrophobic solvent, and a distillation residue (G) comprising substantially a first polyamine fraction, and e) the aqueous phase (H) leaving the extraction stage (4) is guided into a penultimate extraction stage (5) in which there takes place on the countercurrent extraction principle an extraction of the aqueous phase with a solvent phase (J) comprising hydrophobic solvent and auxiliary amine, wherein there results the aqueous phase (K) which is impoverished as to polyamine, and f) the organic phase (L) arising in the extraction stage (5) is at least in part, optionally after passing through a washing stage (8.0), separated in a multi-stage distillation (8.1), (8.2) into a first fraction (M) comprising substantially hydrophobic solvent and optionally proportions of auxiliary amine, and a second fraction (N) comprising substantially auxiliary amine and optionally proportions of hydrophobic solvent, and a distillation residue (O) comprising substantially a second polyamine fraction, and g) the aqueous phase (K) arising in the extraction stage (5) is at least in part, h) optionally at least in part by way of an interposed distillation stage (9), i) guided into an extraction stage (6) and is extracted in countercurrent with an organic phase (P) comprising substantially hydrophobic solvent and optionally as a maximum sufficient auxiliary amine such that there results in (6) an aqueous phase (Q) which, compared with the aqueous phase (K) utilized, is impoverished as to arylamine and which is, k) optionally at least in part by way of an interposed distillation stage (9), l) combined with the optionally present residues of (Q) and (K) and is recycled as stream (C), in that stream (C) is, m) optionally at least in part by way of an interposed extraction stage (3) and/or n) optionally at least in part first by way of an extraction stage (2) positioned upstream and then by way of an optionally present extraction stage (3), o) returned to the extraction stage (4) and is there recycled, optionally after the addition of water and/or auxiliary amine, as stream (C), and p) the organic phase (R) arising in the extraction stage (6) is, optionally after the addition of further organic phase from stream (S), comprising substantially auxiliary amine, supplied to the extraction stage (5) as extraction agent phase (J).

3. The process of claim 2, wherein the recycled stream (C) exhibits a higher degree of protonation than the aqueous phase (K') leaving the extraction stage (4), optionally up to 100%.

4. The process of claim 2, wherein b) the organic phase (D) arising in the extraction stage (4) is at least in part extracted in countercurrent with at least a part volume of the stream (C) in an interposed extraction stage (3) and/or is extracted in countercurrent with at least a part volume of the aqueous phase (Z) arising in the optionally present extraction stage (2) positioned upstream, the aqueous phase (U) resulting in the interposed extraction stage (3) is supplied to the extraction stage (4), and the organic phase (V) arising in the interposed extraction stage (3) is supplied to the working-up stage (7).

5. The process of claim 2, wherein
c) a partial stream of the organic phase (D) leaving the extraction stage (4) and/or a partial stream of the organic phase leaving the optionally present interposed extraction stage (3) is separated and is extracted in countercurrent in an extraction stage (2) positioned upstream with a part volume, preferably with the total volume, of the aqueous phase available as stream (C), the organic stream (W) utilized in the extraction stage (2) is dimensioned such that there takes place in (2) as extensive a transfer as possible of the polyamine contained in the said organic stream into the aqueous phase, the aqueous phase (Z) resulting in the extraction stage (2) positioned upstream is, optionally after the addition of water from stream (Y) and/or auxiliary amine, supplied at least in part to the extraction stage (3), and the organic phase impoverished as to polyamine, which arises in the extraction stage (2) positioned upstream is supplied to the extraction stage (4).

6. The process of claim 2, wherein
k) before its recycling, the aqueous phase (K) leaving the extraction stage (5) is at least in part, and/or before its recycling the aqueous phase (Q) leaving the extraction stage (6) is at least in part liberated by distillation (9) from a part (X) of the water contained therein, the latter is optionally used for washing (7.0) that part of the organic phase (D) leaving the extraction stage (4) and/or of the organic phase (V) leaving the extraction stage (3), which is/are supplied to the working-up (7.1), (7.2) by distillation, and/or for washing (8.0) that part of the organic phase (L) leaving the extraction stage (5), which is supplied to the working-up (8.1), (8.2) by distillation, for the purpose of removing traces of acid, the water (Y) arising thereby is returned at a suitable point into the aqueous phase, the resulting concentrated aqueous phase is combined with the optionally remaining residues of (K) and (Q) and is supplied to recycling as stream (C).

7. The process of claim 2, wherein aniline is used as the auxiliary amine.

8. The process of claim 2, wherein a polyamine mixture of the diphenylmethane series obtained during acid-catalyzed aniline formaldehyde condensation is used as the polyamine mixture.

9. In a process for the preparation of a polyisocyanate by phosgenating an aromatic polyamine, the improvement wherein the polyamine is produced by the process of claim 1.

10. In the preparation of cycloaliphatic polyamines by the hydrogenation of aromatic polyamines, the improvement wherein the aromatic polyamines are produced by the process of claim 1.

* * * * *

UNITED STATES PATENT AND TRADEMARK OFFICE
CERTIFICATE OF CORRECTION

PATENT NO.   :   5,648,520
DATED        :   July 15, 1997
INVENTOR(S)  :   Hartmut Knofel et al It is certified that error appears in the above-indentified patent and that said Letters Patent is hereby corrected as shown below:

On the title page, item [54], correct the title by inserting "MIXTURES" after "POLYAMINE".

At column 1, line 2, in the title, insert "MIXTURES" after "POLYAMINE".

Signed and Sealed this

Fourth Day of November, 1997

*Attest:*

BRUCE LEHMAN

*Attesting Officer*    Commissioner of Patents and Trademarks